United States Patent [19]

Ales et al.

[11] Patent Number: 5,441,055
[45] Date of Patent: Aug. 15, 1995

[54] GUIDEWIRE EXTENSION WIRE AND CONNECTOR ASSEMBLY

[75] Inventors: Francisco Ales, Hialeah; Jack C. Conrad, Plantation; David A. Duvall, Miami; Karl R. Zawoy, Ft. Lauderdale, all of Fla.

[73] Assignee: Cordis Corporation, Miami Lakes, Fla.

[21] Appl. No.: 266,213

[22] Filed: Jun. 27, 1994

[51] Int. Cl.6 .............................................. A61B 17/00
[52] U.S. Cl. ....................................... 128/772; 128/657
[58] Field of Search ................... 128/772, 657; 604/95, 604/264, 280, 281, 282

[56] References Cited

U.S. PATENT DOCUMENTS

| | | |
|---|---|---|
| Re. 34,466 | 12/1993 | Taylor et al. . |
| 3,674,014 | 7/1972 | Tillander ........................ 128/657 |
| 4,827,941 | 5/1989 | Taylor et al. . |
| 4,875,489 | 10/1989 | Messner et al. . |
| 4,907,332 | 3/1990 | Christian et al. . |
| 4,917,103 | 4/1990 | Gambale et al. . |
| 4,922,923 | 5/1990 | Gambale et al. . |
| 4,966,163 | 10/1990 | Kraus et al. . |
| 5,031,636 | 7/1991 | Gambale et al. . |
| 5,035,686 | 7/1991 | Crittenden et al. . |
| 5,060,660 | 10/1991 | Gambale et al. . |
| 5,109,867 | 5/1992 | Twyford . |
| 5,113,872 | 5/1992 | Jahrmarkt et al. . |
| 5,117,838 | 6/1992 | Palmer et al. . |
| 5,133,364 | 7/1992 | Palermo et al. . |
| 5,139,032 | 8/1992 | Jahrmarkt et al. . |
| 5,163,903 | 11/1992 | Crittenden et al. . |
| 5,188,621 | 2/1993 | Samson et al. . |
| 5,191,888 | 3/1993 | Palmer et al. . |
| 5,195,535 | 3/1993 | Shank . |
| 5,195,978 | 3/1993 | Schiffer . |
| 5,197,486 | 3/1993 | Frassica . |
| 5,234,002 | 8/1993 | Chan . |
| 5,234,437 | 8/1993 | Sepetka ....................... 128/772 X |
| 5,246,009 | 9/1993 | Adams ........................ 128/657 X |
| 5,247,942 | 9/1993 | Prather et al. . |
| 5,267,573 | 12/1993 | Evans et al. . |
| 5,271,415 | 12/1993 | Foerster et al. . |
| 5,275,173 | 1/1994 | Samson et al. . |
| 5,281,203 | 1/1994 | Ressemann . |
| 5,282,478 | 2/1994 | Fleischhaker, Jr. et al. . |
| 5,339,833 | 9/1994 | Berthiaume et al. . |
| 5,341,817 | 8/1994 | Viera . |
| 5,341,818 | 8/1994 | Abrams et al. . |

*Primary Examiner*—Sam Rimell
*Attorney, Agent, or Firm*—Thomas R. Vigil

[57] ABSTRACT

The guidewire extension wire and connector assembly comprises: a guidewire extension wire having a distal end portion including, extending toward a distal end of the guidewire extension wire, a break-away neck, a reduced-in-diameter stub section and a larger-in-diameter distal stub end; an inner sleeve having an inner end fixed to the guidewire extension wire proximally of the break-away neck and an outer end extending to the larger-in-diameter distal stub end; an outer sleeve having an inner end thereof fixed to the larger-in-diameter distal stub end; and, a fixing mechanism within an outer end of the outer sleeve adapted to engage a generally cylindrical reduced-in-diameter proximal stub end of an initially inserted guidewire.

18 Claims, 3 Drawing Sheets

GUIDEWIRE EXTENSION WIRE AND CONNECTOR ASSEMBLY

BACKGROUND OF THE INVENTION

1. Field of the Invention

The present invention relates to a guidewire extension wire and connector assembly for connecting to a proximal end of an initially inserted guidewire. The connector assembly can be broken to detach the guidewire extension wire leaving a cylindrical stub section identical to the proximal end of the initially inserted guidewire whereby another, e.g. different length guidewire extension wire and connector assembly, can be connected to the cylindrical stub section.

2. Description of the Related Art Including Information Disclosed Under 37 CFR §§1.97–1.99

Heretofore, a number of guidewire extension wire connector assemblies have been proposed. Several examples of such previously proposed guidewire extension wire connector assemblies are disclosed in the following U.S. Patents:

| U.S. Pat. No. | Patentee |
| --- | --- |
| 4,827,941 | Taylor et al. |
| Re 34,466 | Taylor et al. |
| 4,875,489 | Messner et al. |
| 4,907,332 | Christian et al. |
| 4,917,103 | Gambale et al. |
| 4,922,923 | Gambale et al. |
| 4,966,163 | Kraus et al. |
| 5,031,636 | Gambale et al. |
| 5,035,686 | Crittenden et al. |
| 5,060,660 | Gambale et al. |
| S,109,867 | Twyford |
| 5,113,872 | Jahrmarkt et al. |
| 5,117,838 | Palmer et al. |
| 5,133,364 | Palermo et al. |
| 5,139,032 | Jahrmarkt et al. |
| 5,163,903 | Crittenden et al. |
| 5,188,621 | Samson et al. |
| 5,191,888 | Palmer et al. |
| 5,195,53S | Shank |
| 5,195,978 | Schiffer |
| 5,197,486 | Frassica |
| 5,234,002 | Chan |
| 5,234,407 | Teirstein et al. |
| 5,246,009 | Adams |
| 5,247,942 | Prather et al. |
| 5,255,690 | Keith et al. |
| 5,267,573 | Evans et al. |
| 5,269,759 | Hernandez et al. |
| 5,271,41S | Foerster et al. |
| 5,275,173 | Samson et al. |
| 5,281,203 | Ressemann |
| 5,282,478 | Fleischhaker, Jr. et al. |

These patents describe various types of connector assemblies for connecting an extension guidewire to an initially inserted guidewire. For example:

The Taylor et al. U.S. Pat. No. 4,827,941 and Reissue No. 34,466 show an initially inserted guidewire having a smaller diameter proximal end which is shaped in an undulating or sinusoidal shape. An extension guidewire is provided having a hollow tubing at a distal end. The tapered undulating end of the initially inserted guidewire is inserted within the hollow tubing of the extension guidewire. A friction fit between the tapered undulating section and inner walls of the hollow tubing securely hold the guidewire and extension guidewire in place. The friction fit connection so formed permits the joined guidewires to be separated simply by pushing the guidewires toward each other and then pulling them apart.

The Messner et al. U.S. Pat. No. 4,875,489 shows an extendable guidewire having main and auxiliary sections and a connection which permits the two sections to be joined together and separated simply by pushing the two sections together and pulling them apart. The initially inserted guidewire has a tapered proximal end and the auxiliary section has a connector at a distal end having an inner tubular member and an outer tubular member or sleeve. The tapered proximal end of the main section is inserted within the inner tubular member of the auxiliary section.

The Foerster et al. U.S. Pat. No. 5,271,415 shows a guidewire extension system for connecting an extension wire to a guidewire. The system includes a tubular outer body with a guidewire retention element and an extension wire retention element fixed within the outer body. The retention elements are preferably helically wound wire and form both a right handed thread and a left handed thread within the outer body. The guidewire and extension wire each have tapered ends and a reduced in diameter core and a flattened tip. The tips are threaded into the helical wire in the outer body until the tips from the guidewire and extension wire abut inside the core.

The Schiffer U.S. Pat. No. 5,195,978 discloses a rapid exchange over the wire catheter with a breakaway feature. The catheter has a breakaway element for progressively exposing the guidewire from a proximal end toward a distal end of the catheter in a simple and efficient manner. The breakaway element may be formed as a longitudinally aligned pull strip provided in the catheter guidewire. In an alternative embodiment of the catheter, the catheter is formed of one more tubular segments which are aligned linearly and joined at circumferential tear lines. A segment of the catheter can be broken away from am adjacent segment at one of the circumferential tear lines and then pulled away from the guidewire and discarded. Removal of subsequent portions of the catheter by breaking segments at one of the circumferential tear lines can be repeated until the remaining part of the catheter can be removed without disturbing the position of the guidewire within the person's body.

SUMMARY OF THE INVENTION

According to the present invention there is provided a guidewire extension wire and connector assembly comprising: a guidewire extension wire having a distal end portion including, extending toward a distal end of the guidewire extension wire, a break-away neck connected to the guidewire extension wire, a stub section having a diameter less than an outer diameter of the distal end portion of the guidewire extension wire and being connected to the breakaway neck and a distal stub end having a diameter larger than the diameter of the stub section and being connected to the stub section; a first sleeve having a proximal end fixed to the guidewire extension wire proximally of the break-away neck and having a distal end extending to the distal stub end; a second sleeve having a first end thereof fixed by a first fixing mechanism to the distal stub end and having a second end adapted to be received over a generally cylindrical proximal stub end of an initially inserted guidewire which has a diameter less than the diameter of the initially inserted guidewire; and, a second fixing mechanism within the second end of the second sleeve for fixing the second sleeve to the proximal stub end of the initially inserted guidewire.

Further according to the invention there is provided a method for connecting and disconnecting a guidewire extension wire to a generally cylindrical proximal stub end of an initially inserted guidewire which has a diameter less than the diameter of the initially inserted guidewire for effecting a catheter exchange procedure using a guidewire extension wire and connector assembly, comprising: a guidewire extension wire having a distal end portion including, extending toward a distal end of the guidewire extension wire, a break-away neck connected to the guidewire extension wire, a stub section having a diameter less than an outer diameter of the distal end portion of the guidewire extension wire and being connected to the break-away neck and a distal stub end having a diameter larger than the diameter of the stub section and being connected to the stub section; a first sleeve having an proximal end fixed to the guidewire extension wire proximally of the break-away neck and having a distal end extending to the distal stub end; a second sleeve having a first end thereof fixed by a first fixing mechanism to the distal stub end and having a second end adapted to be received over the proximal stub end of an initially inserted guidewire which has a diameter less than the diameter of the initially inserted guidewire; and, a second fixing mechanism within the second end of the second sleeve for fixing the second sleeve to the proximal stub end of the initially inserted guidewire, the method comprising the steps of: placing the second end of the second sleeve over the proximal stub end of the initially inserted guidewire to fix, with the second fixing mechanism, the second sleeve to the proximal stub end of the initially inserted guidewire; performing a catheter exchange procedure; bending the distal end portion of the guidewire extension wire in the area of the break-away neck to break the guidewire extension wire away from the stub section; and, removing the broken-away guidewire extension wire leaving a new proximal stub end formation defined by the stub section now connected by the distal stub end, the first fixing mechanism, the second sleeve and the second fixing mechanism to the proximal stub end of the initially inserted guidewire.

DESCRIPTION OF THE PREFERRED EMBODIMENT(S)

Figure 1:
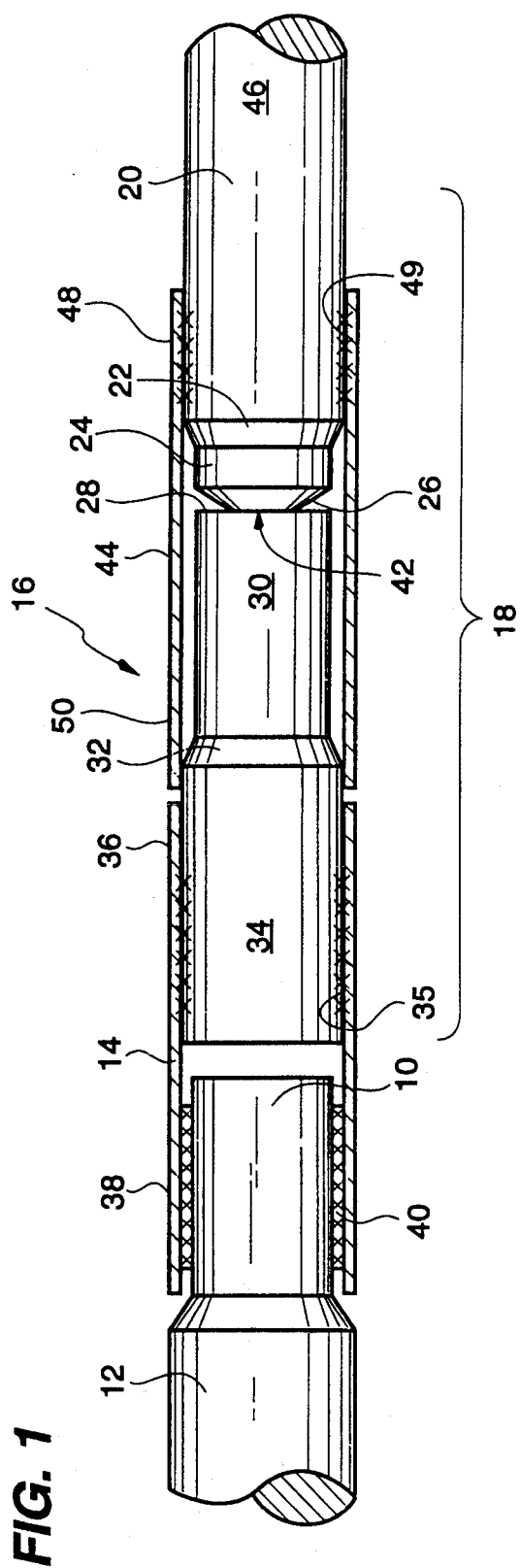
FIG. 1 is a longitudinal view, partially in section and with portions broken away, of a proximal end of an initially inserted guidewire, a distal end of a guidewire extension wire and a connector assembly connecting them together and constructed according to the teachings of the present invention.

Referring now to the drawings in greater detail, there is illustrated in FIG. 1 a proximal end 10 of an initially inserted guidewire 12, the end 10 being a ground down generally cylindrical, reduced-in-diameter stub end 10. A first or outer sleeve or piece of hypo-tube (a short section of tube cut from hypodermic needle material and having an outer diameter (O.D.) of between 0.010 and 0.018 inches) 14 of a connector assembly 16 extends from a distal end portion 18 of a guidewire extension wire 20. The distal end portion 18 is cut down to form a tapered or conical surface 22 which extends distally axially to a short, axially extending reduced-in-diameter portion 24 followed by a sharper tapered cut, defining a tapered or conical surface 26 which extends to a flat axially facing end surface 28 of a reduced-in-diameter stub section 30 which extends distally to an outwardly tapering surface 32 which tapers to a larger-in-diameter cylindrical distal stub end 34 which is fixed, such as by welding or with an adhesive 35 such as contact cement, a cyanoacrylate ester, a thixotropic material or a pressure sensitive adhesive, to the inside of an inner end 36 of the outer sleeve 14.

According to the teachings of the present invention, an outer end 38 of the sleeve 14 is adapted to be received over the reduced-in-diameter proximal stub end 10 of the initially inserted guidewire 12 and fixed thereto by a fixing mechanism 40 which in this embodiment is an adhesive 40. The adhesive 40 can be a cyanoacrylate ester or other type of contact cement.

The junction 42 between the conical surface 26 and the axially facing end surface 28 defines a break-away neck 42.

It will be apparent that the reduced-in-diameter stub section 30 is substantially identical in shape and size as the proximal reduced-in-diameter stub end 10 of the initially inserted guidewire 12.

A second or inner sleeve, or section of hypo-tube 44 is fixed to an outer surface 46 of the guidewire extension wire 20 on the inside of its inner end 48 just proximal of the first tapered or conical surface 22, such as by a welding 49 or with an adhesive 49. An outer end 50 of the second or inner sleeve 44 extends over the reduced-in-diameter stub section 30 and over a proximal margin of the larger-in-diameter stub end 34.

When, in a clinical procedure, a catheter needs to be replaced, the guidewire extension wire 20 and connector assembly 16 can be connected to the proximal cylindrical stub end 10 of the initially inserted guidewire 12 and fixed thereto by the fixing mechanism/adhesive 40. The fixing mechanism/adhesive 40 prevents any relative movement axially or rotationally between the connector assembly 16 and the proximal cylindrical stub end 10 of the initially inserted guidewire 12.

Then the inserted catheter can be made to slide back over the assembly of the initially inserted guidewire 12, the connector assembly 16 and the guidewire extension wire 20 now connected to the proximal cylindrical stub end 10 of the initially inserted guidewire 10 left in place in a blood vessel and a new catheter can be made to slide forward on this created assembly to a desired position.

Figure 2:
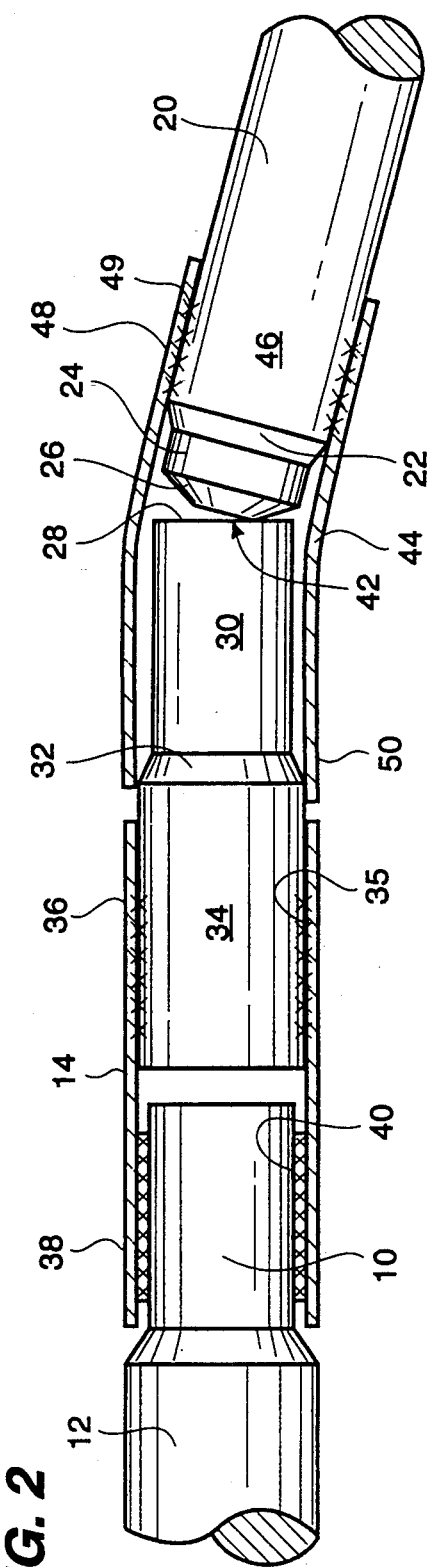
FIG. 2 is a longitudinal view, partially in section and with portions broken away, of the assembly shown in FIG. 1 but with the guidewire extension wire bent to break it away from the connector assembly.
Figure 3:
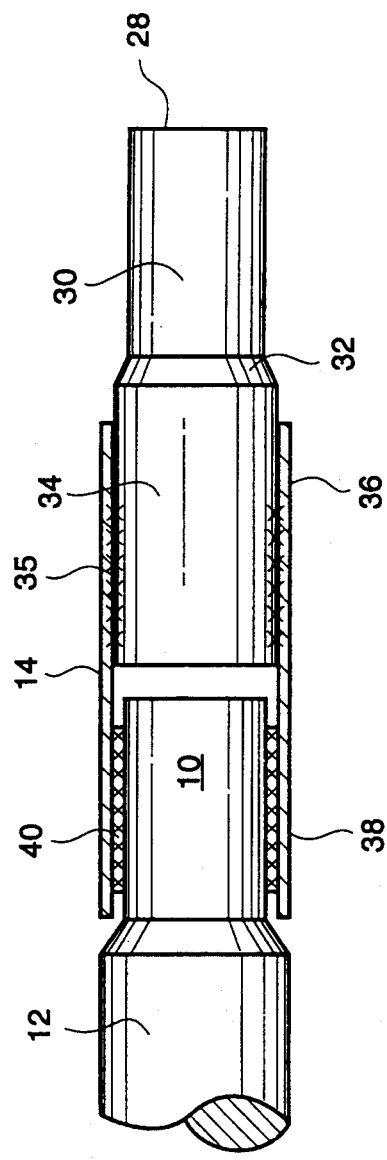
FIG. 3 is a longitudinal view, partially in section and with portions broken away, of the proximal end of the initially inserted guidewire and part of the connector assembly including an axially projecting cylindrical stub section after the broken away part has been removed.

When the catheter exchange procedure is finished, a finger bending force is applied to the connector assembly near the location of the break-away neck 42, i.e., the middle area of the inner sleeve 44, with both hands bending the connector assembly 16 less than 90° to break the distal end portion 18 of the guidewire extension 20 at the break-away neck 42 away from the reduced-in-diameter stub section 30. The break-away neck 42 breaks due to the flexing of the connector assembly 16 and the concentration of the flexing load at the break-away neck 42 causes the break-away neck 42 to break the junction between the stub section 30 and the tapered or conical surface 26 as shown in FIG. 2.

The guidewire extension wire 20 with the inner sleeve 44 is then removed leaving a new assembly of the proximal stub end 10, the outer sleeve 14, the larger-in-diameter stub end 34 and the smaller-in-diameter cylindrical stub section 30, now forming a stub end 30 which is similar in shape as the proximal stub end 10 of the initially inserted guidewire 12.

Figure 4:
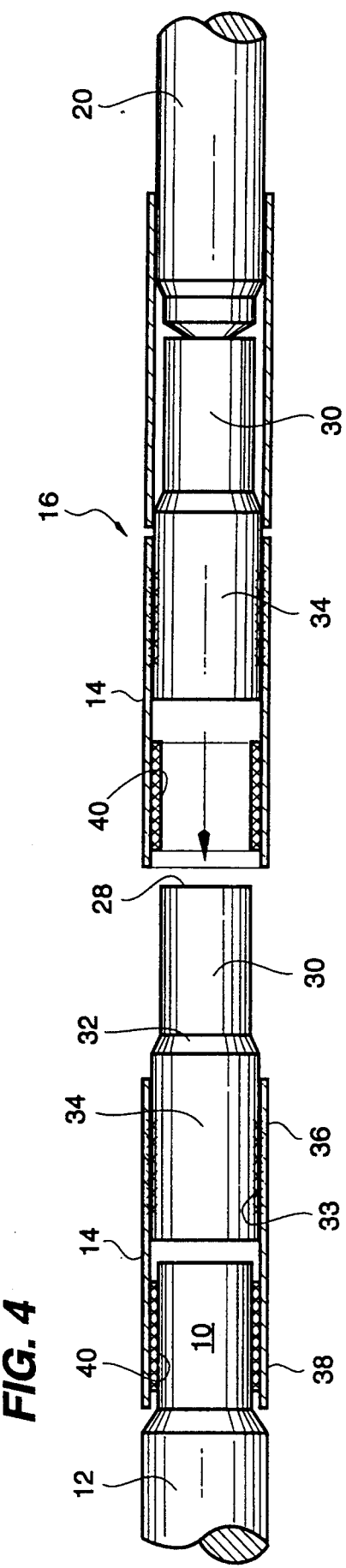
FIG. 4 is a longitudinal view, partially in section and with portions broken away, of the proximal end of the initially inserted guidewire and part of the connector assembly including an axially projecting cylindrical stub section and the connector assembly of another guidewire extension wire positioned to be inserted over the axially projecting cylindrical stub section.

Because of the similarity of the stub section 30 to the stub end 10, the former stub section 30 of the connector assembly 16 becomes a new back end section of the initially inserted guidewire 12. Then, if necessary, a new guidewire extension wire 20 and connector assembly 16 can be connected to the cylindrical stub end 30, as indicated in FIG. 4.

Figure 5:
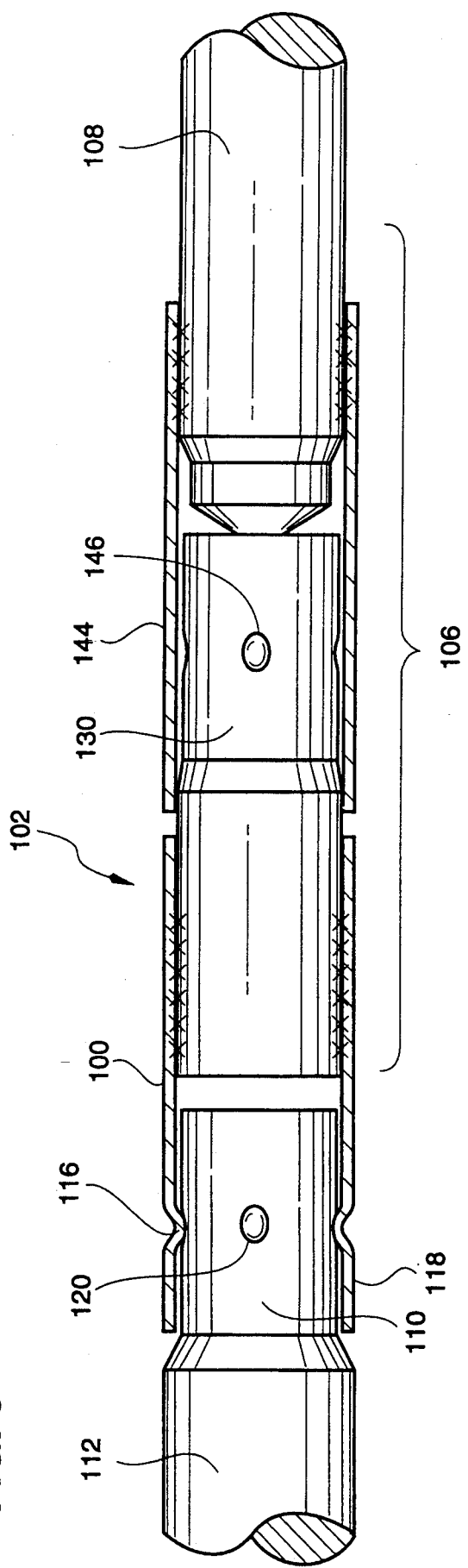
FIG. 5 is a longitudinal view, partially in section and with portions broken away, of a proximal end of an initially inserted guidewire, a distal end of a guidewire extension wire and a connector assembly connecting them together, similar to the view in FIG. 1, but showing a mechanical connection between the proximal end of the initially inserted guidewire and the connector assembly of another guidewire extension wire.

Instead of using a cement or adhesive, a mechanical connection can be made between an outer sleeve 100 of a connector assembly 102 attached to and forming part of a distal end portion 106 of a guidewire extension wire 108 and the cylindrical proximal end 110 of an initially inserted guidewire 112, as shown in FIG. 5.

In FIG. 5, one form of mechanical connection is shown which comprises four radially inwardly extending detents 116 in an outer end 118 of the outer sleeve 100 which are snap-fittingly received, respectively, in four recesses 120 which are formed in the proximal end 110 of the initially inserted guidewire 112. Of course, a stub section 130 in the connector assembly 102 within an inner sleeve 144 of the connector assembly 102 is provided with a similar set of four recesses 146, as shown in FIG. 5.

From the foregoing description, it will be apparent that the guidewire extension wire 20 or 108 and associated connector assembly 16 or 102 of the present invention has a number of advantages, some of which have been described above and others of which are inherent in the invention. Also it will be understood that modifications can be made to the guidewire extension wire 20 or 108 and associated connector assembly 16 or 102 of the present invention described above without departing from the teachings of the present invention. Accordingly, the scope of the invention is only to be limited as necessitated by the accompanying claims.

We claim:

1. A guidewire extension wire and connector assembly comprising:

a guidewire extension wire having a distal end portion including, extending toward a distal end of said guidewire extension wire, a break-away neck connected to said guidewire extension wire, a stub section having a diameter less than an outer diameter of said distal end portion of said guidewire extension wire and being connected to said break-away neck and a distal stub end having a diameter larger than the diameter of said stub section and being connected to said stub section;

a first sleeve having a proximal end fixed to said guidewire extension wire proximally of said break-away neck and having a distal end extending to said distal stub end;

a second sleeve having a first end thereof fixed by a first fixing means to said distal stub end and having a second end adapted to be received over a generally cylindrical proximal stub end of an initially inserted guidewire which has a diameter less than the diameter of the initially inserted guidewire; and, a second fixing means within said second end of said second sleeve for fixing said second sleeve to the proximal stub end of the initially inserted guidewire.

2. The assembly of claim 1 wherein said first fixing means comprises contact cement.

3. The assembly of claim 1 wherein said second fixing means is a mechanical connection between said second end of said second sleeve and the proximal stub end of the initially inserted guidewire and said stub section has the same length and diameter as the length and diameter of the proximal stub end of the initially inserted guidewire for enabling a connection easily to be made to a second guidewire extension wire and connector assembly after said first named guidewire extension wire is broken away from said stub section connected by said distal stub end, said first fixing means, said second sleeve and said second fixing means to the proximal stub end of the initially inserted guidewire.

4. The assembly of claim 1 wherein said break-away neck is defined by a steeply tapered or conical surface extending radially inwardly of the guidewire extension wire within said first sleeve and axially to an end face of said stub section located within said first sleeve.

5. The assembly of claim 1 wherein said guidewire extension wire, said first sleeve and said second sleeve are made of metal.

6. The assembly of claim 1 wherein said guidewire extension wire, said first sleeve and said second sleeve are made of plastic.

7. A method for connecting and disconnecting a guidewire extension wire to a generally cylindrical proximal stub end of an initially inserted guidewire which has a diameter less than the diameter of the initially inserted guidewire for effecting a catheter exchange procedure using a guidewire extension wire and connector assembly, comprising: a guidewire extension wire having a distal end portion including, extending toward a distal end of the guidewire extension wire, a break-away neck connected to said guidewire extension wire, a stub section having a diameter less than an outer diameter of said distal end portion of said guidewire extension wire and being connected to said break-away neck and a distal stub end having a diameter larger than the diameter of said stub section and being connected to said stub section; a first sleeve having an proximal end fixed to said guidewire extension wire proximally of said break-away neck and having a distal end extending to said distal stub end; a second sleeve having a first end thereof fixed by a first fixing means to said distal stub end and having a second end adapted to be received over the proximal stub end of an initially inserted guidewire which has a diameter less than the diameter of the initially inserted guidewire; and, a second fixing means within said second end of said second sleeve for fixing said second sleeve to the proximal stub end of the initially inserted guidewire, said method comprising the steps of:

placing said second end of said second sleeve over said proximal stub end of said initially inserted guidewire to fix, with said second fixing means, said second sleeve to the proximal stub end of the initially inserted guidewire;

performing a catheter exchange procedure;

bending said distal end portion of said guidewire extension wire in the area of the break-away neck to break the guidewire extension wire away from the stub section; and, removing the broken-away guidewire extension wire leaving a new proximal stub end formation defined by the stub section now connected by said distal stub end, said first fixing means, said second sleeve and said second fixing means to the proximal stub end of the initially inserted guidewire.

8. The method of claim 7 including the further step of connecting a second guidewire extension wire and connector assembly to the stub section by inserting the second end of a second sleeve of the second guidewire extension wire and connector assembly over the stub section now connected by said distal stub end, said first fixing means, said second sleeve and said second fixing means to form the new proximal stub end formation for the initially inserted guidewire.

9. The method of claim 7 wherein said guidewire extension wire, said first sleeve and said second sleeve are made of metal.

10. The method of claim wherein said guidewire extension wire, said first sleeve and said second sleeve are made of plastic.

11. The assembly of claim 1 wherein said first fixing means comprises a cyanoacrylate ester.

12. The assembly of claim 1 wherein said first fixing means comprises a thixotropic material.

13. The assembly of claim 1 wherein said first fixing means comprises a pressure sensitive adhesive.

14. The assembly of claim 1 wherein said first fixing means comprises a weldment.

15. The assembly of claim 1 wherein said second fixing means comprises a cyanoacrylate ester.

16. The assembly of claim 1 wherein said second fixing means comprises a thixotropic material.

17. The assembly of claim 1 wherein said second fixing means comprises a pressure sensitive adhesive.

18. The assembly of claim 1 wherein said second fixing means comprises contact cement.

* * * * *

UNITED STATES PATENT AND TRADEMARK OFFICE
CERTIFICATE OF CORRECTION

PATENT NO. : 5,441,055
DATED : August 15, 1995
INVENTOR(S) : Francisco Ales, et al.

It is certified that error appears in the above-indentified patent and that said Letters Patent is hereby corrected as shown below:

Column 1, line 35, "S,109,867" should be --5,109,867--.

Column 1, line 41, "5,195,53S" should be --5,195,535--.

Column 1, line 50, "5,271,41S" should be --5,271,415--.

Column 2, line 35, "one more" should be --one or more--.

Column 2, line 38, "am" should be --an--.

Column 2, line 56, "breakaway " should be --break-away--.

Column 8, line 9, "of claim wherein" should be --of claim 7 wherein--.

Signed and Sealed this

Twenty-eighth Day of November 1995

Attest:

BRUCE LEHMAN

*Attesting Officer*          *Commissioner of Patents and Trademarks*